United States Patent [19]

Rehn et al.

[11] Patent Number: 4,532,346
[45] Date of Patent: Jul. 30, 1985

[54] PROCESS FOR THE PREPARATION OF HYDROXYPHENOXY-ALKANECARBOXYLIC ACIDS

[75] Inventors: Karl Rehn, Hofheim am Taunus; Hans J. Nestler, Königstein, both of Fed. Rep. of Germany

[73] Assignee: Hoechst Aktiengesellschaft, Frankfurt am Main, Fed. Rep. of Germany

[21] Appl. No.: 547,744

[22] Filed: Nov. 1, 1983

[30] Foreign Application Priority Data

Nov. 5, 1982 [DE] Fed. Rep. of Germany ....... 3240805

[51] Int. Cl.³ .............................................. C07C 65/03
[52] U.S. Cl. ...................................... 562/471; 560/61
[58] Field of Search .......................... 560/61; 562/471

[56] References Cited
FOREIGN PATENT DOCUMENTS 2824828  2/1979  Fed. Rep. of Germany ........ 560/61

Primary Examiner—Paul J. Killos
Attorney, Agent, or Firm—Curtis, Morris & Safford

[57] ABSTRACT

Continuous process for the preparation of hydroxy-phenoxy-alkanecarboxylic acids of the formula

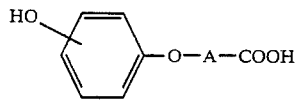

in which A is alkylene, by reaction of dihydroxybenzenes with alpha-haloalkanecarboxylic acids of the formula

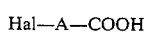

or the derivatives thereof at 80°–120° C. in a reaction tube.

7 Claims, No Drawings

PROCESS FOR THE PREPARATION OF HYDROXYPHENOXY-ALKANECARBOXYLIC ACIDS

Hydroxyphenoxy-alkanecarboxylic acids (I) and their functional derivatives are known as valuable intermediates for the manufacture of dyestuffs and substances active in plant protection (German Offenlegungsschriften Nos. 2,640,730, 2,824,828; see also R. Wegler, Chemie der Pflanzenschutz- und Schädlingsbekämpfungsmittel, vol. 8 (1982), p. 8 et sequ.):

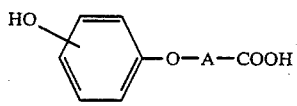   (I)

As bifunctional compounds, monoalkylated dihydroxybenzene derivatives of type I are furthermore important as starting materials for organic synthesis.

In I, A is a methylene group optionally substituted by 1 to 2 alkyl groups having a total of up to 4 carbon atoms; the free hydroxy group being in 2-, 3- or 4-position to the ether oxygen function.

It is known that monoalkylated dihydroxybenzene derivatives are obtainable with difficulty only. In addition to attempts for direct selective alkylation of dihydroxybenzenes under varying reaction conditions such as different temperatures, bases and solvents or differing stoichiometric ratio of the reactants, synthesis using protective groups or via a selective dealkylation of bis-alkylated dihydroxybenzenes has been tried. Important methods of this kind are summarized for example in German Offenlegungsschrift No. 2,824,828. The process of this Offenlegungsschrift relates to another variant of direct alkylation, i.e. the reaction of dihydroxybenzene(hydroquinone) in alcoholic solution with 2-haloalkanecarboxylic acid derivatives. In a rather expensive reaction (with the use of alcoholates) and a complicated work-up, ester derivatives of the acids of type I were thus obtained.

A critical appraisal of the available methods for the preparation of compounds of the formula I shows that they do not meet the requirements of an economic synthesis process applicable for large scale production.

The process of German Offenlegungsschrift No. 2,824,828 gives a satisfactory yield only when using as auxiliary bases alcoholates freshly prepared from alkali metals, which complicates the process and increases the cost therof. This is valid, too, for processes using protective groups. Moreover, the processes according to the state of the art generally require the use of organic solvents, which in addition to increased cost causes problems with respect to disposal of waste water. Furthermore, side reactions reduce the yields, particularly in the process of direct alkylation of dihydroxybenzenes with halocarboxylic acids (or their derivates) in aqueous alkaline solution, where not only undesirable bis-alkylation (reaction at both OH groups) occurs but also continued reaction of the final product I with additional haloalkanecarboxylic acid (or its derivatives), which leads to the formation of addition products of the formula

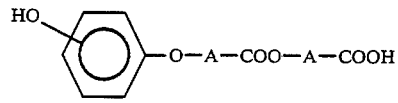

Surprisingly, it has now been found that most of the above disadvantages can be avoided by carrying out the direct alkylation reaction continuously in a flow tube reactor. The subject of the present invention is therefore a process for the preparation of hydroxy-phenoxy-alkanecarboxylic acids of the formula I, in which A is as defined above, which comprises mixing first dihydroxybenzenes of the formula

   II in an aqueous alkaline solution with 2-haloalkanecarboxylic acids of the formula III

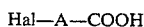   III in which A is as defined above, or the halides or lower alkyl esters thereof, at a temperature of below 60° C., and subsequently passing the mixture continuously through a reaction tube at a temperature of 80° to 120° C.

According to a preferred embodiment of the invention, an aqueous alkaline dihydroxybenzene solutiion and the 2-haloalkanecarboxylic acid in liquid state or in solution are dosed from two separate reservoirs to a mixer in a defined ratio. The mixer the volume of which is as small as possible is provided with efficient cooling means so that the temperature is kept below 60° C. during the mixing of the reactants. At this temperature the reaction does not yet start.

The mixture is introduced into a reactor where it is rapidly heated by means of a heat transfer medium such as pressure water, steam, oil, or electrically to a temperature of from 80° to 120° C., whereby the reaction is started. In some cases, the reaction heat set free is sufficient to keep the reaction going, so that after the start of the reaction further addition of external energy is unnecessary. If the reaction is carried out at atmospheric pressure, the upper temperature limit is determined by the boiling point of the aqueous alkaline solution (about 105° C. in Example 1); however, the temperature may be increased, if desired, by applying pressure (up to about 6 bar).

The quantitative ratio of the reactants and the auxiliary base is especially important in the process of the invention. In order to obtain a maximum yield of monoalkylation product relative to the bis-alkylation product formed simultaneously, it is recommended to use an excess of dihydroxybenzene. Although part of the hydroxybenzene remains in the reaction mixture in unreacted state, unreacted dihydroxybenzene can easily be recovered by suitable work-up methods, for example acidifcation and extraction with appropriate solvents, and then reused. It is advantageous to restrict the excess of dihydroxybenzene because otherwise the amount of salt and that of the solvent required for extraction will become too large. A molar ratio (II:III) of 1:0.3 to 1:0.7 is therefore recommended. At this proportion, the ratio of mono- to bis-alkylation product in the reaction mixture is about (80-95%):(5-20%).

In the case where the bis-alkylation product is undesired, it can be separated from the mono-alkylation product I according to usual methods such as fractional crystallization or derivatization (for example esterification), and subsequent distillation.

As auxiliary base KOH or NaOH are primarily used. For complete conversion at least a stoichiometric amount is required; a slight excess, however, is advantageous. The auxiliary base may be introduced into the mixer in the form of an aqueous solution; or may be added previously to the solution of the dihydroxybenzene (as in the Examples); or may be used completely or portionwise to convert the halocarboxylic acid into its salt and thus be fed into the reaction mixture. In the latter case, care has to be taken to prevent hydrolytic splitting-off of the reactive halogen atom in the reservoir already.

The mixer may be shaped as a vessel with stirrer or as static mixing device. In the latter case it must be ensured that the temperature in the medium does not exceed 60° C. as long as the components are not completely mixed.

The reaction generally proceeds at a temperature of from 80° to 120° C. Depending on the reaction temperature a residence time of the reaction mixture of from 1 to 15 minutes in the reaction chamber is sufficient for complete conversion. Since the dihydroxybenzene is used in excess, the criterion for a terminated reaction is the complete consumption of the 2-haloalkanecarboxylic acid. Surprisingly, it has been observed that when operating according to the process of the invention the halocarboxylic acid reacts only substantially with the dihydroxybenzene despite relatively high reaction temperatures; the known side reactions of 2-haloalkanecarboxylic acids occur only to an insignificant extent.

The reactor is preferably a coiled pipe which may have a length of several hundred meters. Care has to be taken that on operation the reaction solution flows through the reactor without back mixing, so that further reaction of I with the starting product II is prevented. This is ensured by adjusting flow rate and residence time of the reaction mixture to length and diameter of the coiled pipe, either by calculation or simple preliminary tests.

The alkaline reaction solution leaving the reactor is worked up continuously or batchwise according to known methods, one of which is described in Example 1.

Suitable dihydroxybenzenes to be used for the reaction in accordance with the invention are the three isomers pyrocatechol, resorcinol and hydroquinone. Examples of applicable 2-halocarboxylic acid components are 2-chloro- and 2-bromo-acetic, 2-chloro- and 2-bromo-propionic, 2-chloro- and 2-bromo-butyric, 2-chloro- and 2-bromo-isobutyric acid, furthermore the possible isomers of 2-chloro- and 2-bromo-valeric acid. Moreover, higher 2-haloalkanecarboxylic acids may be used as starting substances in the case where the corresponding final products are in demand in the practice.

In all cases where the 2-haloalkanecarboxylic acids exist in the form of their D- and L-(R- and S-) enantiomers, they can be reacted in principle in the same way as the racemates; the reaction at the asymmetric 2-carbon atom proceeding preferably under Walden inversion, thus yielding chiral final products again.

When using acid halides or lower alkyl esters of III as starting substances, the free acids I likewise are formed under the reaction conditions by saponification.

The following Examples illustrate the invention.

EXAMPLE 1

20 ml/min of a solution of 180 g of hydroquinone in 720 g of 25 weight % sodium hydroxide solution and 2 ml/min of 2-chloropropionic acid are simultaneously dosed into a glass tube having a length of 180 mm, an inner diameter of 18 mm and provided with a stirrer which serves as mixer. The mixture then passes into a heatable coiled glass tube having a length of 390 mm and a capacity of 82 ml, which serves as reactor. The temperature of the mixture which rises by about 20° C. in the mixer is increased to 105° C. in the reaction tube. After a residence time of 3.7 minutes the completely reacted mixture is introduced into a continuously operated neutralization vessel, where a pH of 5 to 6 is adjusted by simultaneous addition of dilute hydrochloric acid. Subsequently, the excess hydroquinone is recovered in an extraction column by means of methylisobutylketone in countercurrent.

The aqueous solution is adjusted to pH 1 with further hydrochloric acid, thus setting free the hydroxyphenoxypropionic acid which is taken up in methylisobutylketone. After distillation, an acid of high purity is obtained. After esterification which ethanol the result of a gas chromatography analysis is 85% of 2-(4-hydroxyphenoxy)propionic acid ethyl ester and 8% bis-alkylated compound.

EXAMPLE 2

The reaction is carried out in the same manner at a residence time of 10 minutes with a throughput per hour of 41.5 kg of fresh and 33.5 kg of regenerated hydroquinone, 300 kg of 25 weight % sodium hydroxide solution and 43.5 kg of 2-chloropropionic acid. The mixer is a highspeed flow mixer, the reactor is a tubular heat exchanger. After the work-up as described in Example 1, 71.5 kg of acid per hour are obtained, the ratio of mono- to bis-compound of which is 9:1.

What is claimed is:

1. In a process for the preparation of hydroxyphenoxyalkanecarboxylic acids of the formula

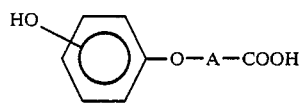

in which A is a methylene group optionally substituted by 1 to 2 alkyl groups having a total of up to 4 carbon atoms, comprising the reaction of a dihydroxybenzene of the formula

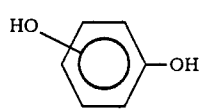

with a 2-haloalkanecarboxylic acid of the formula

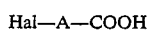

in which A is as defined above, or the halides or lower alkyl esters thereof, the improvement comprising mixing an aqueous alkaline solution of the dihydroxybenzene and the 2-haloalkanecarboxylic acid at a temperature below 60° C., and subsequently passing the aqueous-alkaline mixture of the dihydroxybenzene and 2-haloalkanecarboxylic acid continuously through a reaction tube at a temperature of 80° to 120° C.

2. The process as claimed in claim 1, wherein the molar ratio (II:III) is 1:0.3 to 1:0.7.

3. The process as claimed in claim 1, which comprises using NaOH or KOH as base.

4. The process as claimed in claim 1, which comprises carrying out the reaction under normal pressure and at the boiling temperature of the mixture.

5. The process as claimed in claim 1, which comprises carrying out the reaction under an overpressure of up to 6 bar.

6. The process as claimed in claim 1, wherein the compound II is hydroquinone, the compound III is 2-chloropropionic acid and the base is NaOH.

7. The process as claimed in claim 6, wherein the compound III is L(-)-2-chloropropionic acid.

* * * * *